(12) United States Patent
Gasteyer et al.

(10) Patent No.: US 9,651,305 B2
(45) Date of Patent: *May 16, 2017

(54) LYOPHILIZATION SYSTEM AND METHOD

(71) Applicant: SP Industries, Inc., Warminster, PA (US)

(72) Inventors: Theodore Hall Gasteyer, Naperville, IL (US); Robert Rex Sever, Arlington Heights, IL (US); Balazs Hunek, Chicago, IL (US); Nigel Grinter, Buffalo Grove, IL (US); Melinda Lee Verdone, Hoffman Estates, IL (US)

(73) Assignee: SP Industries, Inc., Warminster, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/943,282

(22) Filed: Nov. 17, 2015

(65) Prior Publication Data

US 2016/0169579 A1    Jun. 16, 2016

Related U.S. Application Data

(63) Continuation of application No. 14/334,722, filed on Jul. 18, 2014, now Pat. No. 9,200,836, which is a continuation of application No. 11/702,479, filed on Feb. 5, 2007, now Pat. No. 8,793,895.

(60) Provisional application No. 60/771,868, filed on Feb. 10, 2006.

(51) Int. Cl.
    *F26B 5/06*     (2006.01)
(52) U.S. Cl.
    CPC ................... *F26B 5/06* (2013.01)

(58) Field of Classification Search
    CPC ........................................... F26B 5/06
    See application file for complete search history.

(56) References Cited

U.S. PATENT DOCUMENTS

| 4,590,684 A | 5/1986 | Arsem |
| 4,597,188 A | 7/1986 | Trappler |
| 5,937,656 A | 8/1999 | Cheng et al. |
| 5,966,966 A | 10/1999 | Botsaris et al. |
| 6,447,701 B1 | 9/2002 | Heschel et al. |
| 6,684,524 B1 | 2/2004 | Sennhenn et al. |
| 8,793,895 B2 | 8/2014 | Gasteyer et al. |
| 9,200,836 B2 * | 12/2015 | Gasteyer, III ............ F26B 5/06 |
| 2002/0031577 A1 | 3/2002 | Arends et al. |

(Continued)

FOREIGN PATENT DOCUMENTS

| GB | 2 400 901 A | 10/2004 |
| WO | WO 9522036 | 8/1995 |
| WO | WO 0109559 A1 | 2/2001 |

OTHER PUBLICATIONS

Argyrios Margaritis, et al., "Principles and Biotechnological Applications", Critical Reviews in Biotechnology, 11(3):277-295 (1991).

(Continued)

*Primary Examiner* — Jiping Lu
(74) *Attorney, Agent, or Firm* — Lowenstein Sandler LLP (57) ABSTRACT

System and method for lyophilization or freeze-drying is provided. During the freezing step, the material or solution to be frozen is initially brought to a temperature near or below its freezing temperature after which the pressure in the freeze-dryer chamber is reduced to induce nucleation of the material.

8 Claims, 4 Drawing Sheets

(56) References Cited

U.S. PATENT DOCUMENTS

2003/0219475 A1 11/2003 Truong-Le
2005/0281737 A1 12/2005 Kuperus et al.
2007/0186567 A1 8/2007 Gasteyer et al.

OTHER PUBLICATIONS

B. Vonnegut, "The Nucleation of Ice Formation by Silver Iodide", Journal of Applied Science, vol. 18, No. 7, Jul. 1947, p. 593-595.
James A. Searles, et al., "The Ice Nucleation Temperature Determines the Primary Drying Rate . . . ", Journal of Pharmaceutical Sciences, vol. 90, No. 7, Jul. 2001, 860-871.
Shailaja Rambhatla, et al., "Heat and Mass Transfer Scale-up Issues during Freeze Drying . . . ", AAPS PhamSciTech 2004; 5 (4) Article 58, pp. 1-9.

\* cited by examiner

LYOPHILIZATION SYSTEM AND METHOD

CROSS-REFERENCE TO RELATED APPLICATIONS

This application is a continuation of U.S. patent application Ser. No. 14/334,722 filed Jul. 18, 2014, now U.S. Pat. No. 9,200,836 issued Dec. 1, 2015, which is a continuation application of U.S. patent application Ser. No. 11/702,479 filed Feb. 5, 2007, now U.S. Pat. No. 8,793,895 issued Aug. 5, 2014, which claims priority to U.S. provisional patent application Ser. No. 60/771,868 filed on Feb. 10, 2006, the disclosures of which are incorporated by reference herein.

FIELD OF THE INVENTION

The present invention relates to a lyophilization process, and more particularly, to a method of inducing nucleation of freezing a material wherein the material is initially cooled to a temperature near or below a phase transition temperature and subsequently de-pressurized so as to induce nucleation of freezing in the material.

BACKGROUND OF THE INVENTION

Controlling the generally random process of nucleation in the freezing stage of a lyophilization or freeze-drying process to both decrease processing time necessary to complete freeze-drying and to increase the product uniformity from vial-to-vial in the finished product would be highly desirable in the art. In a typical pharmaceutical freeze-drying process, multiple vials containing a common aqueous solution are placed on shelves that are cooled, generally at a controlled rate, to low temperatures. The aqueous solution in each vial is cooled below the thermodynamic freezing temperature of the solution and remains in a sub-cooled metastable liquid state until nucleation occurs.

The range of nucleation temperatures across the vials is distributed randomly between a temperature near the thermodynamic freezing temperature and some value significantly (e.g., up to about 30° C.) lower than the thermodynamic freezing temperature. This distribution of nucleation temperatures causes vial-to-vial variation in ice crystal structure and ultimately the physical properties of the lyophilized product. Furthermore, the drying stage of the freeze-drying process must be excessively long to accommodate the range of ice crystal sizes and structures produced by the natural stochastic nucleation phenomenon.

Additives have been used to increase the nucleation temperature of sub-cooled solutions. These additives can take many forms. It is well known that certain bacteria (e.g., *Pseudomonas syringae*) synthesize proteins that help nucleate ice formation in sub-cooled aqueous solutions. Either the bacteria or their isolated proteins can be added to solutions to increase the nucleation temperature. Several inorganic additives also demonstrate a nucleating effect; the most common such additive is silver iodide, AgI. In general, any additive or contaminant has the potential to serve as a nucleating agent. Lyophilization vials prepared in environments containing high particulate levels will generally nucleate and freeze at a lower degree of sub-cooling than vials prepared in low particulate environments.

All the nucleating agents described above are labeled "additives," because they change the composition of the medium in which they nucleate a phase transition. These additives are not typically acceptable or desirable for FDA regulated and approved freeze-dried pharmaceutical products. These additives also do not provide control over the time and temperature when the vials nucleate and freeze. Rather, the additives only operate to increase the average nucleation temperature of the vials.

Ice crystals can themselves act as nucleating agents for ice formation in sub-cooled aqueous solutions. In the "ice fog" method, a humid freeze-dryer is filled with a cold gas to produce a vapor suspension of small ice particles. The ice particles are transported into the vials and initiate nucleation when they contact the fluid interface.

The "ice fog" method does not control the nucleation of multiple vials simultaneously at a controlled time and temperature. In other words, the nucleation event does not occur concurrently or instantaneously within all vials upon introduction of the cold vapor into the freeze-dryer. The ice crystals will take some time to work their way into each of the vials to initiate nucleation, and transport times are likely to be different for vials in different locations within the freeze-dryer. For large scale industrial freeze-dryers, implementation of the "ice fog" method would require system design changes as internal convection devices are required to assist a more uniform distribution of the "ice fog" throughout the freeze-dryer. When the freeze-dryer shelves are continually cooled, the time difference between when the first vial freezes and the last vial freezes will create a temperature difference between the vials, which will increase the vial-to-vial non-uniformity in freeze-dried products.

Vial pre-treatment by scoring, scratching, or roughening has also been used to lower the degree of sub-cooling required for nucleation. As with the other prior art methods, vial pre-treatment also does not impart any degree of control over the time and temperature when the individual vials nucleate and freeze, but instead only increases the average nucleation temperature of all vials.

Vibration has also been used to nucleate a phase transition in a metastable material. Vibration sufficient to induce nucleation occurs at frequencies above 10 kHz and can be produced using a variety of equipment. Often vibrations in this frequency range are termed "ultrasonic," although frequencies in the range 10 kHz to 20 kHz are typically within the audible range of humans. Ultrasonic vibration often produces cavitation, or the formation of small gas bubbles, in a sub-cooled solution. In the transient or inertial cavitation regime, the gas bubbles rapidly grow and collapse, causing very high localized pressure and temperature fluctuations. The ability of ultrasonic vibration to induce nucleation in a metastable material is often attributed to the disturbances caused by transient cavitation. The other cavitation regime, termed stable or non-inertial, is characterized by bubbles that exhibit stable volume or shape oscillations without collapse. U.S. Patent Application 20020031577 A1 discloses that ultrasonic vibration can induce nucleation even in the stable cavitation regime, but no explanation of the phenomenon is offered. GB Patent Application 2400901A also discloses that the likelihood of causing cavitation, and hence nucleation, in a solution using vibrations with frequencies above 10 kHz may be increased by reducing the ambient pressure around the solution or dissolving a volatile fluid in the solution.

An electrofreezing method has also been used in the past to induce nucleation in sub-cooled liquids. Electrofreezing is generally accomplished by delivering relatively high electric fields (~1 V/nm) in a continuous or pulsed manner between narrowly spaced electrodes immersed in a sub-cooled liquid or solution. Drawbacks associated with an electrofreezing process in typical lyophilization applications include the relative complexity and cost to implement and maintain, particularly for lyophilization applications using multiple vials or containers. Also, electrofreezing cannot be directly applied to solutions containing ionic species (e.g., NaCl).

Recently, there are studies that examine the concept of 'vacuum-induced surface freezing' (See e.g., U.S. Pat. No. 6,684,524). In such 'vacuum induced surface freezing', vials containing an aqueous solution are loaded on a temperature controlled shelf in a freeze-dryer and held initially at about 10 degrees Celsius. The freeze-drying chamber is then evacuated to near vacuum pressure (e.g., 1 mbar) which causes surface freezing of the aqueous solutions to depths of a few millimeters. Subsequent release of vacuum and decrease of shelf temperature below the solution freezing point allows growth of ice crystals from the pre-frozen surface layer through the remainder of the solution. A major drawback for implementing this 'vacuum induced surface freezing' process in a typical lyophilization application is the high risk of violently boiling or out-gassing the solution under stated conditions.

Improved control of the nucleation process can enable the freezing of all unfrozen pharmaceutical solution vials in a freeze-dryer to occur within a more narrow temperature and time range, thereby yielding a lyophilized product with greater uniformity from vial-to-vial. Controlling the minimum nucleation temperature can affect the ice crystal structure formed within the vial and allow for a greatly accelerated freeze-drying process.

Therefore, a need exists for controlling the random process of nucleation in various freezing processes including the freezing stage of a freeze-drying or lyophilization process to both decrease processing time necessary to complete freeze-drying and improve the product uniformity from vial-to-vial in the finished product. It would therefore be desirable to provide a process that possesses some, or preferably all, of the above characteristics.

SUMMARY OF THE INVENTION

The present invention may be characterized as a method of lyophilizing a material comprising the steps of: (i) cooling the material in a chamber at a prescribed cooling rate; (ii) decreasing the pressure in the chamber dryer to induce nucleation of freezing in the material; (iii) further cooling the nucleated material to or below a final temperature to freeze the material; and (iv) drying the material to produce a dried product having reduced moisture or solvent.

The invention may also be characterized as a freeze-dryer system comprising: a chamber having a controlled gas atmosphere and one or more shelves adapted to hold one or more containers or vials of a material; a means to control the temperature of the shelves within the chamber so as to control the temperature of the material; a condenser coupled to the chamber and adapted to remove any solvent or moisture from the chamber; and a means to control the pressure of the chamber to rapidly depressurize the chamber to nucleate a phase change in the material during freezing and to maintain a low pressure during drying.

Finally, the invention may be characterized as a method of lyophilizing a material comprising the steps of: (i) bringing the material to a temperature near or below a phase transition temperature in a pressurized gas atmosphere; (ii) decreasing the pressure to nucleate freezing in the material; and (iii) drying the material to produce a dried product having reduced moisture or solvent.

BRIEF DESCRIPTION OF THE DRAWINGS

The above and other aspects, features, and advantages of the present invention will be more apparent from the following, more detailed description thereof, presented in conjunction with the following drawings, wherein.

DETAILED DESCRIPTION OF THE INVENTION

Nucleation is the onset of a phase transition in a small region of a material. For example, the phase transition can be the formation of a crystal from a liquid. The crystallization process (i.e., formation of solid crystals from a solution) often associated with freezing of a solution starts with a nucleation event followed by crystal growth.

In the crystallization process, nucleation is the step where selected molecules dispersed in the solution or other material start to gather to create clusters in the nanometer scale as to become stable under the current operating conditions. These stable clusters constitute the nuclei. The clusters need to reach a critical size in order to become stable nuclei. Such critical size is usually dictated by the operating conditions such as temperature, contaminants, degree of supersaturation, etc. and can vary from one sample of the solution to another. It is during the nucleation event that the atoms in the solution arrange in a defined and periodic manner that defines the crystal structure.

Crystal growth is the subsequent growth of the nuclei that succeed in achieving the critical cluster size. Depending upon the conditions either nucleation or crystal growth may predominate over the other, and as a result, crystals with different sizes and shapes are obtained. Control of crystal size and shape constitutes one of the main challenges in industrial manufacturing, such as for pharmaceuticals.

The present method relates to a process for controlling the time and/or temperature at which a nucleated phase transition occurs in a material. In freezing applications, the probability that a material will spontaneously nucleate and begin changing phase is related to the degree of sub-cooling of the material and the absence or presence of contaminants, additives, structures, or disturbances that provide a site or surface for nucleation.

The freezing or solidification step is particularly important in the freeze-drying process where existing techniques result in nucleation temperature differences across a multitude of vials or containers. The nucleation temperature differences tend to produce a non-uniform product and an excessively long drying time. The present methods, on the other hand, provide a higher degree of process control in batch solidification processes (e.g., freeze-drying) and produce a product with more uniform structure and properties. Unlike some of the prior art techniques to induce nucleation, the present methods require minimal equipment and operational changes for implementation.

In principle, the present methods can be applied to any material processing step that involves a nucleated phase transition. Examples of such processes include the freezing of a liquid, crystallization of ice from an aqueous solution, crystallization of polymers and metals from melts, crystallization of inorganic materials from supersaturated solutions, crystallization of proteins, artificial snow production, deposition of ice from vapor, food freezing, freeze concentration, fractional crystallization, cryopreservation, or condensation of vapors to liquids. From a conceptual standpoint, the present methods may also be applied to phase transitions such as melting and boiling.

The presently disclosed method represents an improvement to current pharmaceutical lyophilization processes. For example, within a large industrial freeze-dryer there can be over 100,000 vials containing a pharmaceutical product that needs to be frozen and dried. Current practice in the industry is to cool the solution to a very high degree so that the solution in all vials or containers in the freeze-dryer are guaranteed to freeze. The content of each vial or container, however, freezes randomly over a range of temperatures below the freezing point, because the nucleation process is uncontrolled.

Figure 1:
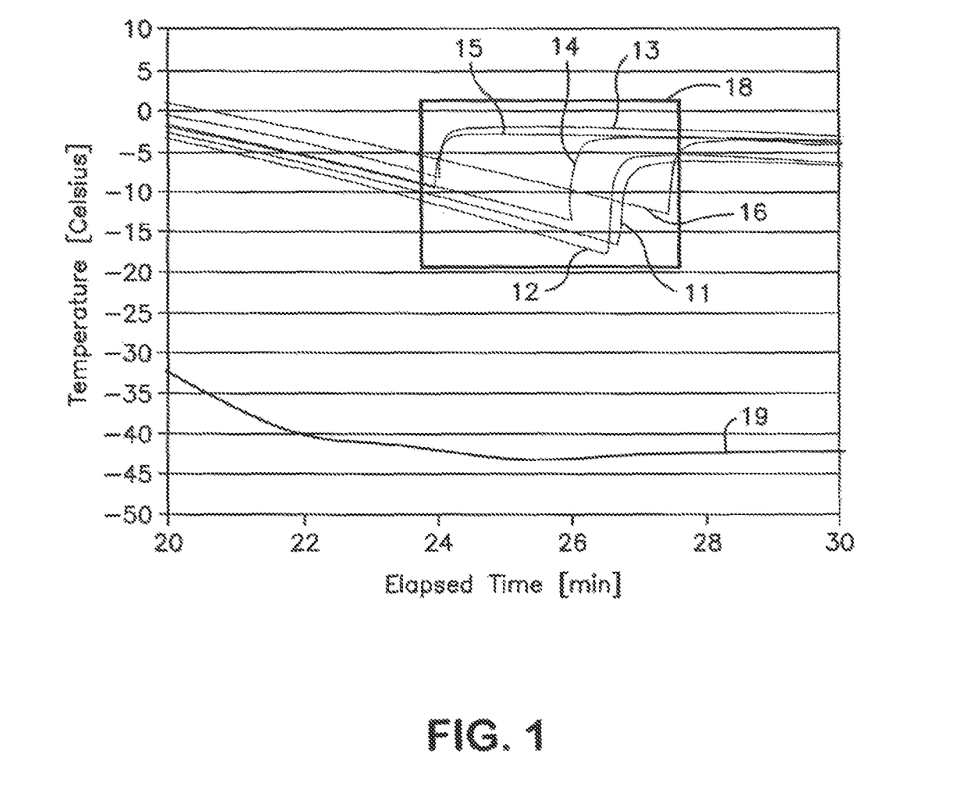
FIG. 1 is a graph depicting the temperature versus time plot of a solution undergoing a stochastic freezing process and further showing the range of nucleation temperatures of the solution.

Turning now to the Figures, and in particular FIG. 1, there is depicted a temperature versus time plot of six vials of an aqueous solution undergoing a conventional stochastic nucleation process showing the typical range of nucleation temperatures of the solution within the vials (11, 12, 13, 14, 15, and 16). As seen therein, the vial contents have a thermodynamic freezing temperature of about 0° C. yet the solution within each vial naturally nucleates over the broad temperature range of about −7° C. to −20° C. or more, as highlighted by area 18. Plot 19 represents the shelf temperature inside the freeze-drying chamber.

Figure 2:
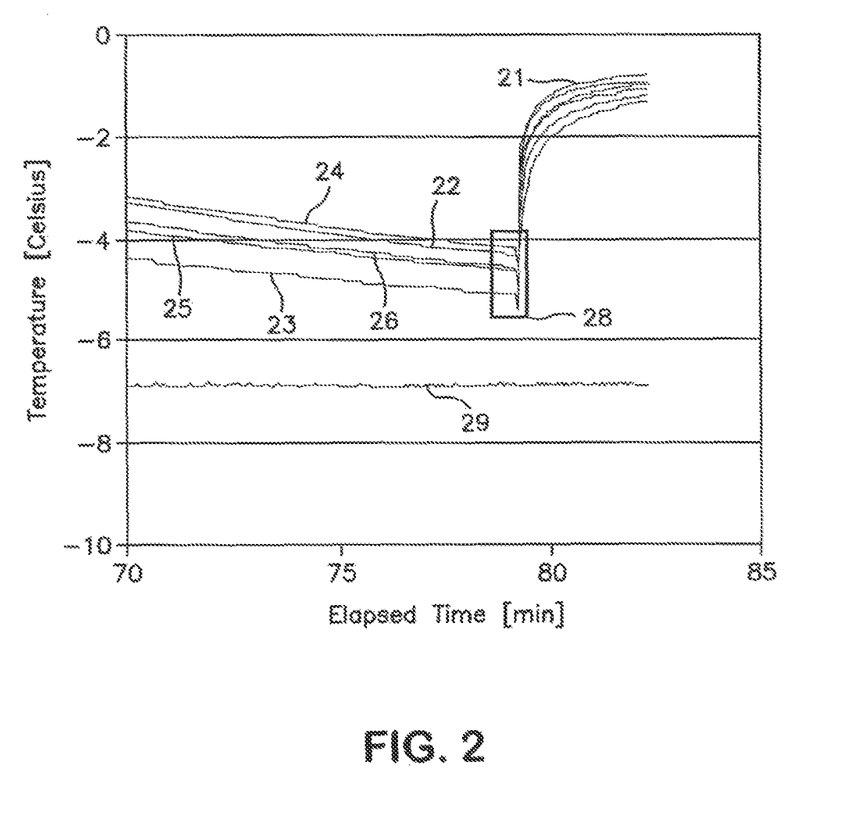
FIG. 2 is a graph depicting the temperature versus time plot of a solution undergoing an equilibrated freezing process with depressurized nucleation in accordance with the present methods.
Figure 3:
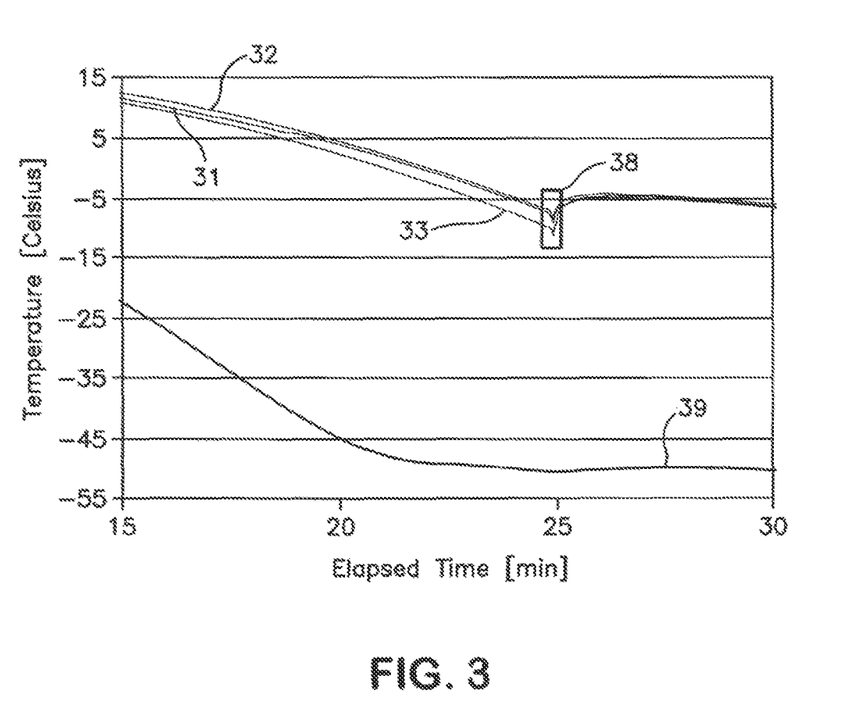
FIG. 3 is a graph depicting the temperature versus time plot of a solution undergoing a dynamic freezing process with depressurized nucleation in accordance with the present methods.

Conversely, FIG. 2 and FIG. 3 depict temperature versus time plots of a solution undergoing a freezing process with depressurized nucleation in accordance with the present methods. In particular, FIG. 2 shows the temperature versus time plot of six vials of an aqueous solution undergoing an equilibrated cooling process (See Example 2) with nucleation induced via depressurization of the chamber (21, 22, 23, 24, 25, and 26). The vial contents have a thermodynamic freezing temperature of about 0° C. yet the solution within each vial nucleates at the same time upon depressurization and within a very narrow temperature range (i.e., −4° C. to −5° C.) as seen in area 28. Plot 29 represents the shelf temperature inside the freeze-drying chamber and depicts an equilibrated freezing process, one where the temperature of the shelves is held more or less steady prior to depressurization.

Similarly, FIG. 3 shows the temperature versus time plot of three vials of an aqueous solution undergoing a dynamic cooling process (See Example 7) with nucleation induced via depressurization of the chamber (31, 32, and 33). Again, the vial contents have a thermodynamic freezing temperature of about 0° C. yet the solution within each vial nucleates at the same time upon depressurization at a temperature range of about −7° C. to −10° C. as seen in area 38. Plot 39 represents the shelf temperature inside the freeze-drying chamber and generally depicts a dynamic cooling process, one where the temperature of the shelves is actively lowered during or prior to depressurization.

As illustrated in the Figures, the present methods provide improved control of the nucleation process by enabling the freezing of pharmaceutical solutions in a freeze-dryer to occur within a more narrow temperature range (e.g., about 0° C. to −10° C.) and/or concurrently, thereby yielding a lyophilized product with greater uniformity from vial-to-vial. While not demonstrated, it is foreseeable that the induced nucleation temperature range may even extend slightly above the phase transition temperature and may also extend to about 40° C. of sub-cooling.

Another benefit associated with the present methods is that by controlling the minimum nucleation temperature and/or the precise time of nucleation one can affect the ice crystal structure formed within the frozen vials or containers. The ice crystal structure is a variable that affects the time it takes for the ice to sublimate. Thus, by controlling the ice crystal structure, it is possible to greatly accelerate the overall freeze-drying process.

Figure 4:
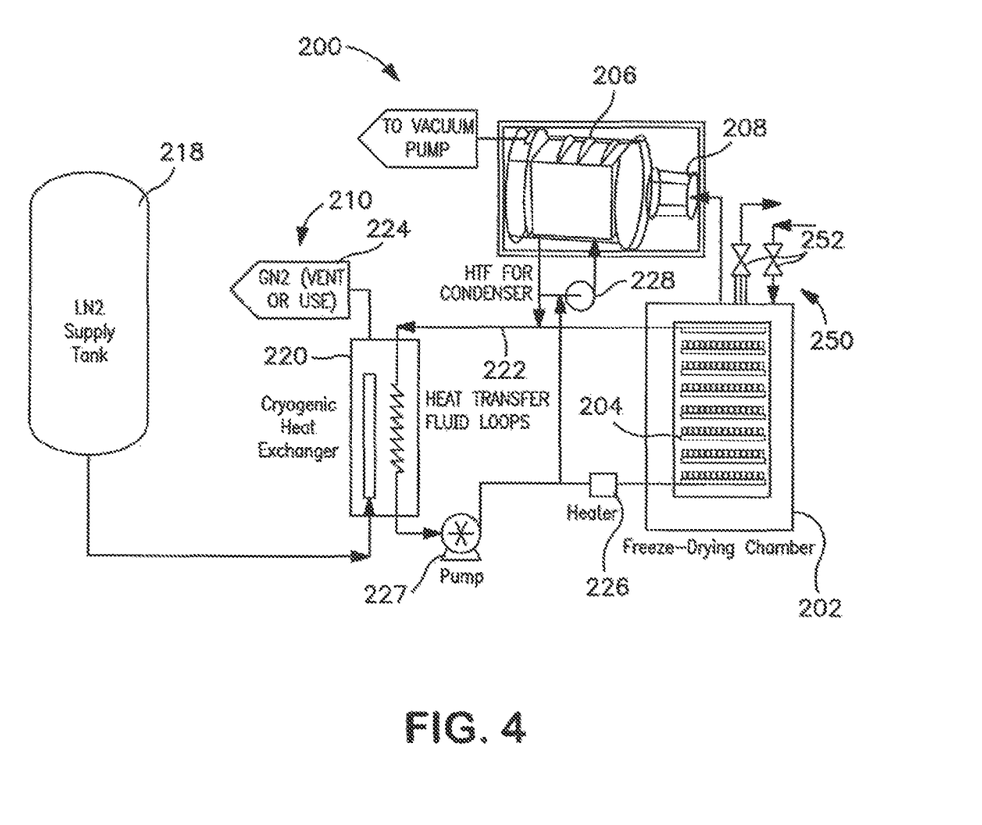
FIG. 4 is a schematic representation of a lyophilization system in accordance with the present invention.

Turning now to FIG. 4, the illustrated freeze-dryer unit (200) has various main components plus additional auxiliary systems to carry out the lyophilization cycle. In particular, the freeze-dryer unit (200) includes a lyophilization chamber (202) that contains the shelves (204) adapted to hold vials or containers of the solution to be lyophilized (not shown). The solution to be lyophilized is specially formulated and typically contains the active ingredient, a solvent system and several stabilization agents or other pharmaceutical acceptable carriers or additives. Lyophilization of this formulation takes place from specialized containers located on hollow shelves. These containers may include vials with stoppers, ampoules, syringes, or, in the case of bulk lyophilization, pans.

The illustrated freeze-dryer unit (200) also includes a condenser (206) that is adapted to remove the sublimated and desorbed solvent from the vapor phase by condensing or freezing it out as ice to maintain adequate vacuum inside the freeze-dryer. The condenser (206) can be internally located in the lyophilization chamber (202) or as a separate external unit in communication with the lyophilization chamber (202) through a so-called isolation valve. The freeze-dryer unit (200) also preferably includes a vacuum pump (208) operatively coupled to the condenser (206) and adapted to pull a vacuum on the lyophilization chamber (202) and condenser (206).

The cryogenic refrigeration system (210) provides the temperature control means for the freeze-dryer unit (200) by cooling a prescribed heat transfer fluid which is circulated to the shelves (204) within the lyophilization chamber (202) and the condenser (206). As illustrated, the cryogenic refrigeration system (210) comprises a source of cryogen (218), such as liquid nitrogen, a cryogenic heat exchanger (220), and a heat transfer fluid circuit (222), a vent (224), a heater (226) and pumps (227,228).

The cryogenic heat exchanger (220) is preferably an NCOOL™ Non-Freezing Cryogenic Heat Exchange System available from Praxair, Inc. An important aspect of the cryogenic heat exchanger (220) is the vaporization of the liquid nitrogen within or internal to the heat exchanger yet in a manner that avoids direct contact of the liquid nitrogen on cooling surfaces exposed to the heat transfer fluid. Details of the structure and operation of such a heat exchanger can be found in U.S. Pat. No. 5,937,656 (Cheng et al.) the disclosure of which is incorporated by reference herein.

The prescribed heat transfer fluid circuit (222) is adapted to circulate a heat transfer fluid and is operatively coupled to both the lyophilization chamber (202) as well as the condenser (206). More specifically, the heat transfer fluid circulates inside the hollow shelves (204) within the lyophilization chamber (202) to precisely communicate the cooling or heating through the shelves (204) to the solution as needed. In addition the prescribed heat transfer fluid also flows through the condenser (206) to provide the cooling means necessary to sublimate the ice and further desorb the solvent.

Pump (227) and heater (226) are disposed along the heat transfer fluid circuit (222) upstream of the lyophilization chamber (202) and downstream of the cryogenic heat exchanger (220). The pump (227) is sized to move the heat transfer fluid through the heat transfer circuit (222) at the require flow rates. The heater (226) is preferably an electric heater adapted to provide supplemental heat to the heat transfer fluid and the lyophilization chamber (202) as may be required during the drying processes.

As seen in the embodiment of FIG. 4, the condenser (206) is also cooled by a recirculation low temperature heat transfer fluid. Refrigeration of the heat transfer fluid flowing through the condenser (206) is also provided by a cryogenic heat exchanger (220). The cryogenic heat exchanger (220) is capable of cooling heat transfer fluid continuously without freezing. During the drying phases, the cryogenic heat exchanger (220) is set or adapted to achieve the lowest temperature required for the condenser (206). As described above, the cryogenic heat exchanger (220) pre-evaporates liquid nitrogen into a cryogenic cold gas for heat transfer to the heat transfer fluid. Through pre-evaporation of the liquid nitrogen assures the liquid nitrogen avoids boiling off directly over a heat exchange surface where the heat transfer fluid is disposed on the other side. Such arrangement avoids freezing of the cryogenic heat exchanger (220) since liquid nitrogen boils at about −195 degrees Centigrade at atmospheric pressure.

The illustrated embodiment of FIG. 4 also includes a means for controlling the gas atmosphere of the lyophilization chamber (250), and in particular the gas composition and pressure within the chamber (202). Controlling the pressure of the chamber (202) allows for the pressurization and rapid depressurization of the chamber to induce nucleation of the solution. The disclosed embodiment preferably uses one or more flow control valves (252) controllably adapted to facilitate the introduction of a pressurized gas atmosphere to the chamber (202) from a source of gas (not shown) and to depressurize the chamber by venting the pressurized gas atmosphere away from the chamber (202) in a controlled and preferably rapid manner thereby inducing the nucleation of the solution in the various containers or vials.

Although not shown, the freeze-dryer unit (200) also includes various control hardware and software systems adapted to command and coordinate the various parts of the freeze-drying equipment, and carry out the pre-programmed lyophilization cycle. The various control hardware and software systems may also provide documentation, data logging, alarms, and system security capabilities as well. In addition, auxiliary systems to the freeze-dryer unit (200) may include various subsystems to clean and sterilize the lyophilization chamber (202), auto-load and unload the product in the lyophilization chamber (202); and associated cryogenic system accessories such as refrigeration skids, liquid nitrogen tanks, piping, valves, sensors, etc.

In a broad sense, the presently disclosed methods for inducing nucleation of a phase transition within a material comprise the steps of: (i) cooling the material to a temperature near or below a phase transition temperature of the material; and (ii) rapidly decreasing the pressure to induce nucleation of a phase transition in the material. Each of these important steps will be discussed in more detail below.

Step 1—Cooling the Material

Illustrative materials useful in the present method include pure substances, gases, suspensions, gels, liquids, solutions, mixtures, or components within a solution or mixture. Suitable materials for use in the present method may include, for example, pharmaceutical materials, biopharmaceutical materials, foodstuffs, chemical materials, and may include products such as wound-care products, cosmetics, veterinary products and in vivo/in vitro diagnostics related products and the like. When the material is a liquid, it may be desirable to dissolve gases into the liquid. Liquids in a controlled gas environment will generally have gases dissolved in them.

Other illustrative materials useful in the present method include biological or biopharmaceutical material such as tissues, organs and multi-cellular structures. For certain biological and pharmaceutical applications, the material may be a solution or mixture that includes: a live or attenuated viruses; nucleic acids; monoclonal antibodies; polyclonal antibodies; biomolecules; nonpeptide analogues; peptides, including polypeptides, peptide mimetics and modified peptides; proteins, including fusion and modified proteins; RNA, DNA and subclasses thereof oligonucleotides; viral particles; and similar such materials or components thereof.

Pharmaceutical or biopharmaceutical solutions contained in vials or containers for freeze-drying would be a good example of a material that would benefit from the present method. The solutions are mostly water and are substantially incompressible. Such pharmaceutical or biopharmaceutical solutions are also highly pure and generally free of particulates that may form sites for nucleation. Uniform nucleation temperature is important to creating a consistent and uniform ice crystal structure from vial to vial or container to container. The ice crystal structure developed also greatly affects the time required for drying.

As applied to a freeze-drying process, the material is preferably placed in a chamber, such as a freeze-drying chamber. Preferably, the chamber is configured so as to allow control of the temperature, pressure, and gas atmosphere within the chamber. The gas atmosphere may include, but is not limited to: argon, nitrogen, helium, air, water vapor, oxygen, carbon dioxide, carbon monoxide, nitrous oxide, nitric oxide, neon, xenon, krypton, methane, hydrogen, propane, butane, and the like, including permissible mixtures thereof. The preferred gas atmosphere comprises an inert gas, such as argon, at a pressure between about 7 to about 50 psig or more. Temperatures within the freeze-dryer chamber are often dictated by the freeze-drying process and are easily controlled via the use of a heat transfer fluid that cools or warms the shelves within the chamber to drive the temperature of the vials or containers and the material within each vial or container.

In accordance with the present methods, the material is cooled to a temperature near or below its phase transition temperature. In the case of an aqueous based solution undergoing a freeze-drying process, the phase transition temperature is the thermodynamic freezing point of the solution. Where the solution reaches temperatures below the thermodynamic freezing point of the solution, it is said to be sub-cooled. When applied to a freezing process of an aqueous-based solution, the present method is effective when the degree of sub-cooling ranges from near or below the phase transition temperature up to about 40° C. of sub-cooling, and more preferably between about 3° C. of sub-cooling and 10° C. of sub-cooling. In some of the examples described below, the present method of inducing nucleation works desirably even where the solution has only about 1° C. of sub-cooling below its thermodynamic freezing point.

Where the material is at a temperature below its phase transition temperature, it is often referred to as being in a metastable state. A metastable state is an unstable and transient, but relatively long-lived, state of a chemical or biological system. A metastable material temporarily exists in a phase or state that is not its equilibrium phase or state. In the absence of any changes in the material or its environment, a metastable material will eventually transition from its non-equilibrium state to its equilibrium state. Illustrative metastable materials include super-saturated solutions and sub-cooled liquids.

A typical example of a metastable material would be liquid water at atmospheric pressure and a temperature of −10° C. With a normal freezing point of 0° C., liquid water should not thermodynamically exist at this temperature and pressure, but it can exist in the absence of a nucleating event or structure to begin the ice crystallization process. Extremely pure water can be cooled to very low temperatures (−30° C. to −40° C.) at atmospheric pressure and still remain in the liquid state. Such sub-cooled water is in a non-equilibrated thermodynamically metastable state. It only lacks a nucleation event to cause it to begin the phase transition whereby it will return to equilibrium.

As discussed above, the present methods of inducing nucleation of a material or freezing a material can be utilized with various cooling profiles, including, for example, an equilibrated cooling environment or a dynamic cooling environment (See FIGS. 2 and 3).

Step 2—Rapidly Decreasing the Pressure

When the material has reached the desired temperature near or below the phase transition temperature, the chamber is quickly or rapidly depressurized. This depressurization triggers the nucleation and phase transition of the solution within the vials or containers. In the preferred embodiment, chamber depressurization is accomplished by opening or partially opening a large control valve that separates the high pressure chamber from either the ambient environment or a lower pressure chamber or environment. The elevated pressure is quickly lowered by mass flow of gas atmosphere out of the chamber. The depressurization needs to be fairly fast to induce the nucleation. The depressurization should be finished in several seconds or less, preferably 40 seconds or less, more preferably 20 seconds or less, and most preferably 10 seconds or less.

In typical freeze-drying applications, the pressure difference between the initial chamber pressure and the final chamber pressure, after depressurization, should be greater than about 7 psi, although smaller pressure drops may induce nucleation in some situations. Most commercial freeze-dryers can readily accommodate the range of pressure drops needed to control nucleation. Many freeze-dryers are designed with pressure ratings in excess of 25 psig to withstand conventional sterilization procedures employing saturated steam at 121° C. Such equipment ratings provide an ample window to induce nucleation following protocols that depressurize from starting pressures above ambient pressure or the pressure in the immediate surrounding environment. The elevated pressure and subsequent depressurization can be achieved through any known means (e.g., pneumatic, hydraulic, or mechanical). In the preferred embodiments, operating pressures for the present methods should remain below the supercritical pressure of any applied gas, and subjecting the material to extreme low pressures (i.e., about 10 mTorr or less) should be avoided during nucleation of the material.

While not wishing to be bound to any particular mechanism, one possible mechanism to explain the controlled nucleation observed in the practice of the present method is that gases in solution in the material come out of solution upon depressurization and form bubbles that nucleate the material. An initial elevated pressure increases the concentration of dissolved gas in the solution. The rapid decrease in pressure after cooling reduces the gas solubility, and the subsequent release of gas from the sub-cooled solution triggers nucleation of the phase transition.

Another possible mechanism is that the temperature decrease of the gas proximate the material during depressurization causes a cold spot on the surface of the material that initiates nucleation. Another possible mechanism is that the depressurization causes evaporation of some liquid in the material and the resultant cooling from the endothermic evaporation process may initiate the nucleation. Another possible mechanism is that the depressurized cold gas proximate the material freezes some vapor either in equilibrium with the material prior to depressurization or liberated from the material by evaporation during depressurization; the resultant solid particles re-enter the material and act as seeds or surfaces to initiate nucleation. One or more of these mechanisms may contribute to initiation of nucleation of freezing or solidification to differing extents depending on the nature of the material, its environment and the phase transition being nucleated.

The process may be carried out entirely at a pressure greater than ambient pressure or over a range of pressures spanning ambient pressure. For example, initial chamber pressure can be above ambient pressure and the final chamber pressure, after depressurization, can be above ambient pressure but less than the initial chamber pressure; the initial chamber pressure can be above ambient pressure and the final chamber pressure, after depressurization, can be about ambient pressure or slightly below ambient pressure.

The rate and magnitude of the pressure drop are also believed to be an important aspect of the present methods. Experiments have shown that nucleation will be induced where the pressure drop ($\Delta P$) is greater than about 7 psi. Alternatively, the magnitude of the pressure drop may be expressed as an absolute pressure ratio, $R=P_i/P_f$, where $P_i$ is initial absolute pressure and $P_f$ is final absolute pressure. It is believed that nucleation may be induced upon depressurization where the absolute pressure ratio, R, is greater than about 1.2 in many practical applications of the present methods. The rate of pressure drop also plays an important role in the present methods. One method of characterizing the rate of pressure drop is through use of a parameter, A, where $A=\Delta P/\Delta t$. Again, it is surmised that nucleation will be induced for values of A greater than a prescribed value, such as about 0.2 psi/sec. Empirical data through experimentation should aid one to ascertain the preferred pressure drop and rate of pressure drop.

The following examples highlight various aspects and features of the presently disclosed methods of inducing nucleation in a material and are not to be taken in a limiting sense. Rather, these examples are illustrative only and the scope of the invention should be determined only with respect to the claims, appended hereto.

EXAMPLES

All examples described herein were performed in a pilot-scale VirTis 51-SRC freeze-dryer having four shelves with approximately 1.0 m² total shelf space and an internal condenser. This unit was retrofitted to hold positive pressures of up to about 15 psig. A 1.5" diameter circular opening also was added to the rear wall of the freeze-drying chamber with 1.5" diameter stainless steel tubing extending from the hole through the rear wall insulation to emerge from the back of the freeze-dryer. Two 1.5" full-port, air-actuated ball valves were attached to this tubing via sanitary fittings. One ball valve allowed gas to flow into the freeze-drying chamber and thereby provide positive pressures up to 15 psig. The second ball valve allowed gas to flow out of the freeze-drying chamber and thereby reduce chamber pressure to atmospheric conditions (0 psig). All refrigeration of the freeze-dryer shelves and condenser was accomplished via circulation of Dynalene MV heat transfer fluid cooled by liquid nitrogen using the Praxair NCool™-HX system.

All solutions were prepared in a class 100 clean room. The freeze-dryer was positioned with the door, shelves, and controls all accessible from the clean room while the other components (pumps, heaters, etc.) were located in a non-clean room environment. All solutions were prepared with HPLC grade water (Fisher Scientific, filtered through 0.10 μm membrane). The final solutions were filtered through a 0.22 μm membrane prior to filling the vials or lyophilization containers. All gases were supplied via cylinders and were filtered through 0.22 μm filters to remove particulates. The glass containers (5 mL vials and 60 mL bottles) were obtained pre-cleaned for particulates from Wheaton Science Products. Pharmaceutically acceptable carriers were used where appropriate. The above steps were taken to ensure the materials and methods met conventional pharmaceutical manufacturing standards for particulates, which act as nucleating agents.

As used herein, "pharmaceutically acceptable carrier" includes any and all solvents, dispersion media, antioxidants, salts, coatings, surfactants, preservatives (e.g., methyl or propyl p-hydroxybenzoate, sorbic acid, antibacterial agents, antifungal agents), isotonic agents, solution retarding agents (e.g., paraffin), absorbents (e.g., kaolin clay, bentonite clay), drug stabilizers (e.g., sodium lauryl sulphate), gels, binders (e.g., syrup, acacia, gelatin, sorbitol, tragacanth, polyvinyl pyrrolidone, carboxy-methyl-cellulose, alginates), excipients (e.g., lactose, milk sugar, polyethylene glycol), disintegration agent (e.g., agar-agar, starch, lactose, calcium phosphate, calcium carbonate, alginic acid, sorbitol, glycine), wetting agents (e.g., cetyl alcohol, glycerol monostearate), lubricants, absorption accelerators (e.g., quaternary ammonium salts), edible oils (e.g., almond oil, coconut oil, oily esters or propylene glycol), sweetening agents, flavoring agents, coloring agents, fillers, (e.g., starch, lactose, sucrose, glucose, mannitol), tabletting lubricants (e.g., magnesium stearate, starch, glucose, lactose, rice flower, chalk), carriers for inhalation (e.g., hydrocarbon propellants), buffering agents, or such like materials and combinations thereof, as would be known to one of ordinary skill in the art.

For the experimental conditions described herein and all lyophilization formulations studied, stochastic nucleation was typically observed to occur at container temperatures between about −8° C. and −20° C. and occasionally as warm as −5° C. The containers could generally be held at temperatures warmer than −8° C. for long periods of time without nucleating. The onset of nucleation and subsequent crystal growth (i.e., freezing) was determined by temperature measurement as the point at which the container temperature quickly increased in response to the exothermic latent heat of fusion. The initiation of freezing also could be visually determined through a sight-glass on the freeze-dryer chamber door.

Example 1

Controlling the Nucleation Temperature

Four separate vials were filled with 2.5 mL of 5 wt % mannitol solution. The predicted thermodynamic freezing point of the 5 wt % mannitol solution is approximately −0.5° C. The four vials were placed on a freeze-dryer shelf in close proximity to one another. The temperatures of the four vials were monitored using surface mounted thermocouples. The freeze-dryer was pressurized with argon to 14 psig.

The freeze-dryer shelf was cooled to obtain vial temperatures of between approximately −1.3° C. and about −2.3° C. (+/−1° C. measurement accuracy of the thermocouples). The freeze-dryer was then depressurized from about 14 psig to about atmospheric pressure in less than five seconds to induce nucleation of the solution within the vials. All four vials nucleated and began freezing immediately after depressurization. Results are summarized in Table 1 below.

As seen in Table 1, the controlled nucleation temperatures in this example (i.e., Initial Vial Temperatures) are quite close to the predicted thermodynamic freezing point of the solution. Thus the present method allows control of the nucleation to occur in solutions that have a very low degree of sub-cooling or at nucleation temperatures near or only slightly colder than their freezing points.

TABLE 1

Controlling the Nucleation Temperature.

| Vial # | Solution | Atmos | Initial Vial Temperature [° C.] | Pressure Drop [psi] | Depressurization Outcome |
|---|---|---|---|---|---|
| 1 | 2.5 mL of 5 wt % mannitol | Argon | −2.3 | 14 | Nucleation |
| 2 | 2.5 mL of 5 wt % mannitol | Argon | −1.3 | 14 | Nucleation |
| 3 | 2.5 mL of 5 wt % mannitol | Argon | −2.1 | 14 | Nucleation |
| 4 | 2.5 mL of 5 wt % mannitol | Argon | −1.7 | 14 | Nucleation |

Example 2

Controlling the Nucleation Temperature

In this example, ninety-five vials were filled with 2.5 mL of 5 wt % mannitol solution. The thermodynamic freezing point of the 5 wt % mannitol solution is approximately −0.5° C. The ninety-five vials were placed on a freeze-dryer shelf in close proximity to one another. The temperature of six vials positioned at different locations in the freeze-dryer shelf was continuously monitored using surface mounted thermocouples. The freeze-dryer was pressurized in an argon atmosphere to about 14 psig. The freeze-dryer shelf was then cooled to obtain vial temperatures of near −5° C. The freeze-dryer was then depressurized from about 14 psig to about atmospheric pressure in less than five seconds to induce nucleation of the solution within the vials. All ninety-five vials were visually observed to nucleate and begin freezing immediately after depressurization. Thermocouple data for the six monitored vials confirmed the visual observation. The results are summarized in Table 2.

As seen therein, controlled nucleation temperatures in this example (i.e., Initial Vial Temperatures) are somewhat below the predicted thermodynamic freezing point of the solution. Thus the present method allows control of the nucleation to occur in solutions that have a moderate degree of sub-cooling. This example also demonstrates scalability of the present method to a multiple vial application.

TABLE 2

Controlling the Nucleation Temperature.

| Vial # | Solution | Atmos | Initial Vial Temperature [° C.] | Pressure Drop [psi] | Depressurization Outcome |
|---|---|---|---|---|---|
| 1 | 2.5 mL of 5 wt % mannitol | Argon | −4.2 | 14 | Nucleation |
| 2 | 2.5 mL of 5 wt % mannitol | Argon | −4.4 | 14 | Nucleation |
| 3 | 2.5 mL of 5 wt % mannitol | Argon | −4.6 | 14 | Nucleation |
| 4 | 2.5 mL of 5 wt % mannitol | Argon | −4.4 | 14 | Nucleation |
| 5 | 2.5 mL of 5 wt % mannitol | Argon | −4.6 | 14 | Nucleation |
| 6 | 2.5 mL of 5 wt % mannitol | Argon | −5.1 | 14 | Nucleation |

Example 3

Controlling the Depressurization Magnitude

In this example, multiple vials were filled with 2.5 mL of 5 wt % mannitol solution. Again, the predicted thermodynamic freezing point of the 5 wt % mannitol solution is approximately −0.5° C. For each test run, the vials were placed on a freeze-dryer shelf in close proximity to one another. As with the earlier described examples, the temperatures of vials were monitored using surface mounted thermocouples. The argon atmosphere in the freeze-dryer was pressurized to differing pressures and the freeze-dryer shelf was cooled to obtain vial temperatures of about −5° C. In each test run, the freeze-dryer was then rapidly (i.e., in less than five seconds) depressurized from the selected pressure to atmospheric pressure in an effort to induce nucleation of the solution within the vials. Results are summarized in Table 3.

As seen in Table 3, the controlled nucleation occurred where the pressure drop was about 7 psi or greater and the nucleation temperature (i.e., initial vial temperature) was between about −4.7° C. and −5.8° C.

Example 4

Controlling the Depressurization Rates

For this example, multiple vials were filled with about 2.5 mL of 5 wt % mannitol solution having a predicted thermodynamic freezing point of approximately −0.5° C. For each test run of varying depressurization time, the vials were placed on a freeze-dryer shelf in close proximity to one another. As with the earlier described examples, the temperatures of vials were monitored using surface mounted thermocouples. Like the above-described examples, the argon atmosphere in the freeze-dryer was pressurized to about 14 psig and the shelf was cooled to obtain vial temperatures of approximately −5° C. In each test run, the freeze-dryer was then depressurized at different depressurization rates from 14 psig to atmospheric pressure in an effort to induce nucleation of the solution within the vials.

To study the effect of depressurization rate or depressurization time, a restricting ball valve was placed on the outlet of the depressurization control valve at the rear of the freeze-dryer. When the restricting valve is completely open, depressurization from about 14 psig to about 0 psig is accomplished in approximately 2.5 seconds. By only partially closing the restricting valve, it is possible to variably increase the chamber depressurization time. Using the restricting ball valve, several test runs were performed with the freeze-dryer chamber depressurized at differing rates to ascertain or determine the effect of depressurization rate on nucleation. The results are summarized in Table 4.

TABLE 3

Effect of Depressurization Magnitude

| Vial # | Solution | Atmos | Initial Vial Temperature [° C.] | Pressure Drop [psi] | Depressurization Outcome |
|---|---|---|---|---|---|
| 1 | 2.5 mL of 5 wt % mannitol | Argon | −4.7 | 7 | Nucleation |
| 2 | 2.5 mL of 5 wt % mannitol | Argon | −5.1 | 7 | Nucleation |
| 3 | 2.5 mL of 5 wt % mannitol | Argon | −5.3 | 7 | Nucleation |
| 4 | 2.5 mL of 5 wt % mannitol | Argon | −5.6 | 7 | No Nucleation |
| 5 | 2.5 mL of 5 wt % mannitol | Argon | −5.6 | 7 | Nucleation |
| 6 | 2.5 mL of 5 wt % mannitol | Argon | −5.8 | 7 | Nucleation |
| 7 | 2.5 mL of 5 wt % mannitol | Argon | −5.4 | 6 | No Nucleation |
| 8 | 2.5 mL of 5 wt % mannitol | Argon | −5.7 | 6 | No Nucleation |
| 9 | 2.5 mL of 5 wt % mannitol | Argon | −5.8 | 6 | No Nucleation |
| 10 | 2.5 mL of 5 wt % mannitol | Argon | −5.1 | 5 | No Nucleation |
| 11 | 2.5 mL of 5 wt % mannitol | Argon | −5.4 | 5 | No Nucleation |
| 12 | 2.5 mL of 5 wt % mannitol | Argon | −5.5 | 5 | No Nucleation |
| 13 | 2.5 mL of 5 wt % mannitol | Argon | −4.7 | 4 | No Nucleation |
| 14 | 2.5 mL of 5 wt % mannitol | Argon | −5.1 | 4 | No Nucleation |
| 15 | 2.5 mL of 5 wt % mannitol | Argon | −5.3 | 4 | No Nucleation |

TABLE 4

Effect of Depressurization Time

| Vial # | Solution | Atmos | Initial Vial Temperature [° C.] | Pressure Drop [psi] | Time [sec] | Depressurization Outcome |
|---|---|---|---|---|---|---|
| 1 | 2.5 mL of 5 wt % mannitol | Argon | −4.6 | 14 | 300 | No Nucleation |
| 2 | 2.5 mL of 5 wt % mannitol | Argon | −5.4 | 14 | 300 | No Nucleation |
| 3 | 2.5 mL of 5 wt % mannitol | Argon | −5.8 | 14 | 300 | No Nucleation |
| 4 | 2.5 mL of 5 wt % mannitol | Argon | −4.6 | 14 | 200 | No Nucleation |
| 5 | 2.5 mL of 5 wt % mannitol | Argon | −5.4 | 14 | 200 | No Nucleation |
| 6 | 2.5 mL of 5 wt % mannitol | Argon | −5.4 | 14 | 200 | No Nucleation |
| 7 | 2.5 mL of 5 wt % mannitol | Argon | −4.6 | 14 | 100 | No Nucleation |
| 8 | 2.5 mL of 5 wt % mannitol | Argon | −5.2 | 14 | 100 | No Nucleation |
| 9 | 2.5 mL of 5 wt % mannitol | Argon | −5.2 | 14 | 100 | No Nucleation |
| 10 | 2.5 mL of 5 wt % mannitol | Argon | −4.7 | 14 | 60 | No Nucleation |
| 11 | 2.5 mL of 5 wt % mannitol | Argon | −5.1 | 14 | 60 | No Nucleation |
| 12 | 2.5 mL of 5 wt % mannitol | Argon | −5.1 | 14 | 60 | No Nucleation |
| 13 | 2.5 mL of 5 wt % mannitol | Argon | −5.1 | 14 | 50 | No Nucleation |
| 14 | 2.5 mL of 5 wt % mannitol | Argon | −5.3 | 14 | 50 | No Nucleation |
| 15 | 2.5 mL of 5 wt % mannitol | Argon | −4.9 | 14 | 50 | No Nucleation |
| 16 | 2.5 mL of 5 wt % mannitol | Argon | −5.4 | 14 | 42 | No Nucleation |
| 17 | 2.5 mL of 5 wt % mannitol | Argon | −5.5 | 14 | 42 | No Nucleation |
| 18 | 2.5 mL of 5 wt % mannitol | Argon | −5.0 | 14 | 42 | No Nucleation |
| 19 | 2.5 mL of 5 wt % mannitol | Argon | −5.1 | 14 | 32 | Nucleation |
| 20 | 2.5 mL of 5 wt % mannitol | Argon | −5.7 | 14 | 32 | Nucleation |
| 21 | 2.5 mL of 5 wt % mannitol | Argon | −5.6 | 14 | 32 | Nucleation |
| 22 | 2.5 mL of 5 wt % mannitol | Argon | −4.7 | 14 | 13 | Nucleation |
| 23 | 2.5 mL of 5 wt % mannitol | Argon | −5.3 | 14 | 13 | Nucleation |
| 24 | 2.5 mL of 5 wt % mannitol | Argon | −5.5 | 14 | 13 | Nucleation |

As seen in Table 4, nucleation only occurred where the depressurization time was less than 42 seconds, the pressure drop was about 14 psi or greater and the nucleation temperature (i.e., initial vial temperature) was between about −4.6° C. and about −5.8° C. These results indicate that the depressurization needs to be accomplished relatively quickly for the method to be effective.

Example 5

Controlling the Gas Atmosphere

Again, multiple vials were each filled with about 2.5 mL of 5 wt % mannitol solution and placed on a freeze-dryer shelf in close proximity to one another. As with earlier described examples, the temperature of the test vials were monitored using surface mounted thermocouples. For the different test runs, the gas atmosphere in the freeze-dryer was varied always maintaining a positive pressure of about 14 psig. In this example, the freeze-dryer shelf was cooled to obtain vial temperatures of approximately −5° C. to −7° C. In each test run, the freeze-dryer was then rapidly depressurized from about 14 psig to atmospheric pressure in an effort to induce nucleation of the solution within the vials. The results are summarized in Table 5.

As seen therein, controlled nucleation occurred in all gas atmospheres except for helium gas atmosphere where the pressure drop was about 14 psi and the nucleation temperature (i.e., initial vial temperature) was between about −4.7° C. and about −7.4° C. Although not shown in the examples, it is believed that alternate conditions will likely enable controlled nucleation in a helium atmosphere.

TABLE 5

Effect of Gas Atmosphere Composition

| Vial # | Solution | Atmos | Initial Vial Temperature [° C.] | Pressure Drop [psi] | Depressurization Outcome |
|---|---|---|---|---|---|
| 1 | 2.5 mL of 5 wt % mannitol | Argon | −4.9 | 14 | Nucleation |
| 2 | 2.5 mL of 5 wt % mannitol | Argon | −5.2 | 14 | Nucleation |
| 3 | 2.5 mL of 5 wt % mannitol | Nitrogen | −4.7 | 14 | Nucleation |
| 4 | 2.5 mL of 5 wt % mannitol | Nitrogen | −5.1 | 14 | Nucleation |
| 5 | 2.5 mL of 5 wt % mannitol | Xenon | −4.8 | 14 | Nucleation |
| 6 | 2.5 mL of 5 wt % mannitol | Xenon | −5.0 | 14 | Nucleation |
| 7 | 2.5 mL of 5 wt % mannitol | Air | −7.4 | 14 | Nucleation |
| 8 | 2.5 mL of 5 wt % mannitol | Air | −7.2 | 14 | Nucleation |
| 9 | 2.5 mL of 5 wt % mannitol | Helium | −5.8 | 14 | No Nucleation |
| 10 | 2.5 mL of 5 wt % mannitol | Helium | −5.5 | 14 | No Nucleation |

Example 6

Large Volume Solutions

In this example, six lyophilization bottles (60 mL capacity) were filled with about 30 mL of 5 wt % mannitol solution having a predicted thermodynamic freezing point of approximately −0.5° C. The six lyophilization bottles were placed on a freeze-dryer shelf in close proximity to one another. The temperature of six bottles positioned at different locations in the freeze-dryer shelf was monitored using surface mounted thermocouples. The freeze-dryer was pressurized in an argon atmosphere to about 14 psig. The freeze-dryer shelf was then cooled to obtain bottle temperatures of near −5° C. The freeze-dryer was then depressurized from 14 psig to about atmospheric pressure in less than five seconds to induce nucleation of the solution within the bottles. The results are summarized in Table 6.

In a separate experiment, a plastic bulk freeze-drying tray (Gore LYOGUARD, 1800 mL capacity) was filled with about 1000 mL of 5 wt % mannitol solution. The tray was obtained pre-cleaned to meet USP low particulate requirements. The tray was placed on a freeze-dryer shelf, and the temperature of the tray was monitored by a thermocouple mounted on the exterior surface of the tray near the center of one side. The freeze-dryer shelf was then cooled to obtain a tray temperature of near −7° C. The freeze-dryer was then depressurized from 14 psig to about atmospheric pressure in less than five seconds to induce nucleation of the solution within the tray. The results are also summarized in Table 6.

Like the above-described examples, all containers nucleated and began freezing immediately after depressurization. Also like the above-described examples, the nucleation temperatures (i.e., Container Temperatures) in this example were very much controllable to be somewhat near the thermodynamic freezing temperature of the solution. More importantly, this example illustrates that the present method allows control of the nucleation to occur in larger volume solutions and various container formats. It should be noted that one would expect the efficacy of the depressurization method to improve as formulation volume increases, because the nucleation event is more likely to occur when more molecules are present to aggregate and form critical nuclei.

TABLE 6

Effect of Solution Volume and Container Type

| Container | Solution | Atmos | Container Temperature [° C.] | Pressure Drop [psi] | Depressurization Outcome |
|---|---|---|---|---|---|
| Bottle #1 | 30 mL of 5 wt % mannitol | Argon | −5.3 | 14 | Nucleation |
| Bottle #2 | 30 mL of 5 wt % mannitol | Argon | −5.1 | 14 | Nucleation |
| Bottle #3 | 30 mL of 5 wt % mannitol | Argon | −5.9 | 14 | Nucleation |
| Bottle #4 | 30 mL of 5 wt % mannitol | Argon | −5.2 | 14 | Nucleation |
| Bottle #5 | 30 mL of 5 wt % mannitol | Argon | −5.9 | 14 | Nucleation |
| Bottle #6 | 30 mL of 5 wt % mannitol | Argon | −6.1 | 14 | Nucleation |
| Tray | 1000 mL of 5 wt % mannitol | Argon | −6.9 | 14 | Nucleation |

Example 7

Dynamic Cooling vs. Equilibrated Cooling

The present methods of controlling nucleation can be used in various modes. Examples 1-6, described above, each demonstrate the aspect of controlling the nucleation temperature of a lyophilization solution that is essentially equilibrated at a temperature below its thermodynamic freezing point (i.e., very slowly changing temperature). This example demonstrates that nucleation can also occur at a temperature below the thermodynamic freezing point in a dynamic cooling environment (i.e., the solution is undergoing rapid changes in temperature).

In this example, vials 1 through 6 represent the samples described above with reference to Example 2. In addition, three separate vials (Vials 7-9) were also filled with 2.5 mL of 5 wt % mannitol solution. In a separate test run, the three additional vials were placed on a freeze-dryer shelf in close proximity to one another. The freeze-dryer shelf was cooled rapidly towards a final shelf temperature of −45° C. When one of the vials reached a temperature of about −5° C., as measured by the surface mounted thermocouples, the freeze-dryer was depressurized rapidly from about 14 psig to 0 psig in an effort to induce nucleation. All three vials nucleated and began freezing immediately after depressurization. The vial temperatures decreased significantly to between −6.8° C. and −9.9° C. prior to nucleation as a result of the dynamic cooling environment. Comparative results are summarized in Table 7 below.

TABLE 7

Test Results - Effect of Dynamic Cooling on Nucleation

| Vial # | Solution | Mode | Nucleation Temp [° C.] | Pressure Drop [psi] | Depressurization Outcome |
|---|---|---|---|---|---|
| 1 | 2.5 mL of 5 wt % mannitol | Equilibrated | −4.2 | 14 | Nucleation |
| 2 | 2.5 mL of 5 wt % mannitol | Equilibrated | −4.4 | 14 | Nucleation |
| 3 | 2.5 mL of 5 wt % mannitol | Equilibrated | −4.6 | 14 | Nucleation |
| 4 | 2.5 mL of 5 wt % mannitol | Equilibrated | −4.4 | 14 | Nucleation |
| 5 | 2.5 mL of 5 wt % mannitol | Equilibrated | −4.6 | 14 | Nucleation |
| 6 | 2.5 mL of 5 wt % mannitol | Equilibrated | −5.1 | 14 | Nucleation |
| 7 | 2.5 mL of 5 wt % mannitol | Dynamic | −6.8 | 14 | Nucleation |
| 8 | 2.5 mL of 5 wt % mannitol | Dynamic | −7.2 | 14 | Nucleation |
| 9 | 2.5 mL of 5 wt % mannitol | Dynamic | −9.9 | 14 | Nucleation |

The efficacy of the present methods for controlling nucleation in lyophilization solutions equilibrated in a given temperature range or lyophilization solutions being dynamically cooled, provides the end-user with two potential modes of application with different benefits and trade-offs. By allowing the lyophilization solutions to equilibrate, the range of nucleation temperatures will be narrow or minimized to the performance limits of the freeze-dryer itself. The equilibration step may require extra time to achieve relative to conventional or dynamic freezing protocols where the chamber and vial temperatures are dropped to less than about −40° C. in one step. However, employing the equilibration step should yield much improved nucleation uniformity across all vials or containers as well as realization of the other benefits associated with precisely controlling the nucleation temperature of the material.

Alternatively, if equilibrating the material or lyophilization solution temperatures is undesirable, one may simply implement the depressurization step at an appropriate time during the normal freezing or dynamic cooling protocol. Depressurization during a dynamic cool down will produce a wider spread in nucleation temperatures for the material within the lyophilization containers, but will add minimal time to the freezing protocol and still allow one to mitigate the problems of extreme sub-cooling.

Example 8

Effect of Different Excipients

The present method of controlling or inducing nucleation in a material can be used to control the nucleation temperature of sub-cooled solutions containing different lyophilization excipients. This example demonstrates the use of the present methods with the following excipients: mannitol; hydroxyethyl starch (HES); polyethylene glycol (PEG); polyvinyl pyrrolidone (PVP); dextran; glycine; sorbitol; sucrose; and trehalose. For each excipient, two vials were filled with 2.5 mL of a solution containing 5 wt % of the excipient. The vials were placed on a freeze-dryer shelf in close proximity to one another. The freeze-dryer was pressurized in an argon atmosphere to about 14 psig. The freeze-dryer shelf was cooled to obtain vial temperatures near −3° C. and then depressurized rapidly to induce nucleation. Results are summarized in Table 8.

TABLE 8

Effect of Different Lyophilization Excipients

| Vial # | Solution/Excipient | Atmos | Initial Vial Temperature [° C.] | Pressure Drop [psi] | Depressurization Outcome |
|---|---|---|---|---|---|
| 1 | 2.5 mL of 5 wt % mannitol | Argon | −3.3 | 14 | Nucleation |
| 2 | 2.5 mL of 5 wt % mannitol | Argon | −3.0 | 14 | Nucleation |
| 3 | 2.5 mL of 5 wt % HES | Argon | −3.1 | 14 | Nucleation |
| 4 | 2.5 mL of 5 wt % HES | Argon | −3.7 | 14 | Nucleation |
| 5 | 2.5 mL of 5 wt % PEG | Argon | −3.8 | 14 | Nucleation |
| 6 | 2.5 mL of 5 wt % PEG | Argon | −3.4 | 14 | Nucleation |
| 7 | 2.5 mL of 5 wt % PVP | Argon | −3.5 | 14 | Nucleation |
| 8 | 2.5 mL of 5 wt % PVP | Argon | −3.3 | 14 | Nucleation |
| 9 | 2.5 mL of 5 wt % dextran | Argon | −4.0 | 14 | Nucleation |
| 10 | 2.5 mL of 5 wt % dextran | Argon | −3.1 | 14 | Nucleation |
| 11 | 2.5 mL of 5 wt % glycine | Argon | −3.8 | 14 | Nucleation |
| 12 | 2.5 mL of 5 wt % glycine | Argon | −3.9 | 14 | Nucleation |
| 13 | 2.5 mL of 5 wt % sorbitol | Argon | −3.6 | 14 | Nucleation |
| 14 | 2.5 mL of 5 wt % sorbitol | Argon | −3.4 | 14 | Nucleation |
| 15 | 2.5 mL of 5 wt % sucrose | Argon | −3.3 | 14 | Nucleation |
| 16 | 2.5 mL of 5 wt % sucrose | Argon | −3.4 | 14 | Nucleation |
| 17 | 2.5 mL of 5 wt % trehalose | Argon | −3.7 | 14 | Nucleation |
| 18 | 2.5 mL of 5 wt % trehalose | Argon | −3.1 | 14 | Nucleation |

Example 9

Controlling Nucleation of Protein Solutions

The present methods and system disclosed herein can be used to control the nucleation temperature of sub-cooled protein solutions without negative or adverse effects on protein solubility or enzymatic activity. Two proteins, bovine serum albumin (BSA) and lactate dehydrogenase (LDH) were used in this example.

BSA was dissolved in 5 wt % mannitol at a concentration of 10 mg/mL. Three lyophilization vials were filled with 2.5 mL of the BSA-mannitol solution and placed on a freeze-dryer shelf in close proximity to one another. The freeze-dryer was pressurized in an argon atmosphere to about 14 psig. The freeze-dryer shelf was cooled to obtain vial temperatures near −5° C. The freeze-dryer was depressurized rapidly to induce nucleation. All vials of BSA solution nucleated and began freezing immediately after depressurization. No precipitation of the protein was observed upon thawing.

The LDH proteins were obtained from two different suppliers and for purposes of clarity are designated as LDH-1 or LDH-2 to distinguish the two distinct batches. LDH-1 was dissolved in 5 wt % mannitol at a concentration of 1 mg/mL. Six lyophilization vials were filled with 2.5 mL of the LDH-1/mannitol solution and placed on a freeze-dryer shelf in close proximity to one another. The freeze-dryer was pressurized in an argon atmosphere to about 14 psig. The freeze-dryer shelf was cooled starting from room temperature to obtain vial temperatures near −4° C. The freeze-dryer was then depressurized rapidly to induce nucleation. All vials nucleated and began freezing immediately after depressurization. The vials were held at this state for about 15 minutes. The freeze-dryer shelf was then cooled at a rate of approximately 1° C./min to obtain vial temperatures near −45° C. and held for an additional 15 minutes to ensure completion of the freezing process. After the freezing step, the freeze-dryer shelf was then warmed at a rate of about 1° C./min to raise the vial temperatures to near 5° C. No precipitation of the protein was observed upon thawing. The vial contents were assayed for enzymatic activity, and the results were compared to a control sample of unfrozen LDH-1/mannitol solution.

As part of Example 9, the depressurized nucleated samples of the LDH-1/mannitol solution were compared to stochastically nucleated samples. In the stochastically nucleated samples of LDH-1, the freezing procedure was repeated without pressurization and depressurization and without the argon atmosphere. Specifically, LDH-1 was dissolved in 5 wt % mannitol at a concentration of 1 mg/mL. Six lyophilization vials were filled with 2.5 mL of the LDH-1/mannitol solution and placed on a freeze-dryer shelf in close proximity to one another. The freeze-dryer shelf was cooled starting from room temperature at a rate of about 1° C./min to obtain vial temperatures near −45° C. and held for 15 minutes to ensure completion of the freezing process. After the freezing step, the freeze-dryer shelf was warmed at a rate of about 1° C./min to raise the vial temperatures to near 5° C. No precipitation of the protein was observed upon thawing. The vial contents were assayed for enzymatic activity, and the results were compared to the same control sample of unfrozen LDH-1/mannitol solution.

Also as part of Example 9, the experiments described above for LDH-1 were repeated using LDH-2. The only difference was a controlled nucleation temperature near −3° C. for LDH-2 rather than −4° C. for LDH-1.

TABLE 9

Controlling the Nucleation Temperature of Sub-Cooled Protein Solutions

| Vial # | Solution | Atmos | Initial Vial Temperature [° C.] | Pressure Drop [psi] | Enzyme Activity Loss[%] | Depressurization Outcome |
|---|---|---|---|---|---|---|
| 1 | 2.5 mL of BSA solution | Argon | −4.9 | 14 | — | Nucleation |
| 2 | 2.5 mL of BSA solution | Argon | −4.3 | 14 | — | Nucleation |
| 3 | 2.5 mL of BSA solution | Argon | −5.3 | 14 | — | Nucleation |
| 4 | 2.5 mL of LDH-1 solution | Argon | −3.8 | 14 | 9.0 | Nucleation |
| 5 | 2.5 mL of LDH-1 solution | Argon | −4.0 | 14 | 16.2 | Nucleation |
| 6 | 2.5 mL of LDH-1 solution | Argon | −3.7 | 14 | 18.4 | Nucleation |
| 7 | 2.5 mL of LDH-1 solution | Argon | −4.0 | 14 | 23.4 | Nucleation |
| 8 | 2.5 mL of LDH-1 solution | Argon | −3.9 | 14 | 18.5 | Nucleation |
| 9 | 2.5 mL of LDH-1 solution | Argon | −4.0 | 14 | 21.2 | Nucleation |
| 10 | 2.5 mL of LDH-1 solution | Air | −10.4 | 0 | 35.7 | Nucleation |
| 11 | 2.5 mL of LDH-1 solution | Air | −16.5 | 0 | 35.4 | Nucleation |
| 12 | 2.5 mL of LDH-1 solution | Air | −15.5 | 0 | 36.1 | Nucleation |
| 13 | 2.5 mL of LDH-1 solution | Air | −10.5 | 0 | 43.9 | Nucleation |
| 14 | 2.5 mL of LDH-1 solution | Air | −9.8 | 0 | 24.9 | Nucleation |
| 15 | 2.5 mL of LDH-1 solution | Air | −11.0 | 0 | 39.2 | Nucleation |
| 16 | 2.5 mL of LDH-2 solution | Argon | −3.1 | 14 | 29.9 | Nucleation |
| 17 | 2.5 mL of LDH-2 solution | Argon | −2.9 | 14 | 18.9 | Nucleation |
| 18 | 2.5 mL of LDH-2 solution | Argon | −3.1 | 14 | 23.3 | Nucleation |
| 19 | 2.5 mL of LDH-2 solution | Argon | −2.7 | 14 | 19.6 | Nucleation |
| 20 | 2.5 mL of LDH-2 solution | Argon | −3.1 | 14 | 32.1 | Nucleation |
| 21 | 2.5 mL of LDH-2 solution | Argon | −2.6 | 14 | 35.2 | Nucleation |
| 22 | 2.5 mL of LDH-2 solution | Air | −5.0 | 0 | 38.3 | Nucleation |
| 23 | 2.5 mL of LDH-2 solution | Air | −5.5 | 0 | 40.0 | Nucleation |
| 24 | 2.5 mL of LDH-2 solution | Air | −2.3 | 0 | 36.5 | Nucleation |
| 25 | 2.5 mL of LDH-2 solution | Air | −3.8 | 0 | 42.0 | Nucleation |
| 26 | 2.5 mL of LDH-2 solution | Air | −5.1 | 0 | 50.2 | Nucleation |
| 27 | 2.5 mL of LDH-2 solution | Air | −5.9 | 0 | 40.6 | Nucleation |

As seen in Table 9, the controlled nucleation and freezing process achieved via depressurization clearly does not decrease enzymatic activity relative to a comparable stochastic nucleation and freezing protocol. In fact, the controlled nucleation process achieved via depressurization appears to better preserve enzyme activity with a mean activity loss of only 17.8% for LDH-1 and 26.5% for LDH-2 compared to the mean activity loss of 35.9% for LDH-1 and 41.3% for LDH-2 after stochastic nucleation.

It should be noted that the stochastic nucleation temperatures observed for LDH-2 were substantially warmer than the stochastic nucleation temperatures for LDH-1. This difference may be due to some contaminant acting as a nucleating agent in the LDH-2. The stochastic nucleation temperatures are much closer to the controlled nucleation temperatures for LDH-2 compared to LDH-1, yet the improvements in retention of enzyme activity obtained via controlled nucleation for LDH-1 and LDH-2 are similar at 18.1% and 14.8%, respectively. This result suggests that the improvements in retention of enzyme activity can be partially attributed to the characteristics of the controlled nucleation process itself, not just to the prescribed warmer nucleation temperatures obtained via depressurization.

Example 10

Reducing Primary Drying Time

A 5 wt % mannitol solution was prepared by mixing about 10.01 grams of mannitol with about 190.07 grams of water. Vials were filled with 2.5 mL of the 5 wt % mannitol solution. The vials were weighed empty and with the solution to determine the mass of water added to the vials. The twenty vials were placed in a rack on a freeze-dryer shelf in close proximity to one another. The temperatures of six vials were monitored using surface mounted thermocouples; all monitored vials were surrounded by other vials to improve uniformity of vial behavior. The freeze-dryer was pressurized to about 14 psig in a controlled gas atmosphere of argon gas. The freeze-dryer shelf was cooled from room temperature to about −6° C. to obtain vial temperatures of between approximately −1° C. and −2° C. The freeze-dryer was then depressurized from about 14 psig to about atmospheric pressure in less than five seconds to induce nucleation of the solution within the vials. All vials observed visually or monitored via thermocouples nucleated and began freezing immediately after depressurization.

The shelf temperature was then lowered rapidly to about −45° C. to complete the freezing process. Once all vial temperatures were about −40° C. or less, the freeze-drying chamber was evacuated and the process of primary drying (i.e., sublimation) was initiated. During this drying process, the freeze-dryer shelf was warmed to about −14° C. via a one hour ramp and held at that temperature for 16 hours. The condenser was maintained at about −60° C. throughout the drying process. Primary drying was stopped by turning off the vacuum pump and backfilling the chamber with argon to atmospheric pressure. The vials were promptly removed from the freeze-dryer and weighed to determine how much water was lost during the primary drying process.

In a separate experiment as part of Example 10, other vials were filled with 2.5 mL of the same 5 wt % mannitol solution. The vials were weighed empty and with the solution to determine the mass of water added to the vials. The vials were loaded into the freeze-dryer in the same manner described above, and the temperatures of six vials were once again monitored using surface-mounted thermocouples. The freeze-dryer shelf was cooled rapidly from room temperature to about −45° C. to freeze the vials. Nucleation occurred stochastically between about −15° C. and about −18° C. during the cooling step. Once all vials temperatures were about −40° C. or less, the vials were dried in a manner identical to the method described above. Upon conclusion of primary drying, the samples were promptly removed from the freeze-dryer and weighed to determine how much water was lost during the primary drying process.

TABLE 10

Increasing the Nucleation Temperature Improves Primary Drying

| Vial # | Solution | Atmos | Initial Vial Temp [° C.] | Pressure Drop [psi] | Water Loss [%] | Depressurized Outcome |
|---|---|---|---|---|---|---|
| 1 | 2.5 mL of 5 wt % mannitol | Argon | −1.3 | 14 | 89.9 | Nucleation |
| 2 | 2.5 mL of 5 wt % mannitol | Argon | −1.9 | 14 | 85.2 | Nucleation |
| 3 | 2.5 mL of 5 wt % mannitol | Argon | −1.3 | 14 | 87.1 | Nucleation |
| 4 | 2.5 mL of 5 wt % mannitol | Argon | −2.3 | 14 | 88.8 | Nucleation |
| 5 | 2.5 mL of 5 wt % mannitol | Argon | −2.1 | 14 | 85.0 | Nucleation |
| 6 | 2.5 mL of 5 wt % mannitol | Argon | −1.1 | 14 | 80.7 | Nucleation |
| 7 | 2.5 mL of 5 wt % mannitol | Air | −15.7 | 0 | 65.7 | — |
| 8 | 2.5 mL of 5 wt % mannitol | Air | −16.7 | 0 | 66.9 | — |
| 9 | 2.5 mL of 5 wt % mannitol | Air | −14.5 | 0 | 64.6 | — |
| 10 | 2.5 mL of 5 wt % mannitol | Air | −15.6 | 0 | 64.7 | — |
| 11 | 2.5 mL of 5 wt % mannitol | Air | −16.5 | 0 | 64.1 | — |
| 12 | 2.5 mL of 5 wt % mannitol | Air | −17.9 | 0 | 65.7 | — |

Results of the freeze-drying process with controlled nucleation and stochastic nucleation are summarized in Table 10 below. It should be noted that these two experiments only differ in the addition of the controlled nucleation via depressurization step to one experiment. As seen in Table 10, the controlled nucleation process achieved via depressurization allows nucleation at very low degrees of sub-cooling, between about −1.1° C. and −2.3° C. in this example. The much warmer nucleation temperatures for the controlled nucleation case compared to the stochastic nucleation case yields an ice structure and resultant lyophilized cake with dramatically improved drying properties. For the same amount of drying time, the vials nucleated using the disclosed depressurization methods between about −1.1° C. and −2.3° C. lost an average of 86.1% of their water while the vials nucleated stochastically between about −14.5° C. and −17.9° C. only lost an average of 65.3%. Hence, the vials nucleated stochastically would require much more primary drying time to achieve the same degree of water loss as the vials nucleated in a controlled manner in accordance with the presently disclosed methods. The improvement in drying time is likely attributed to the formation of larger ice crystals at warmer nucleation temperatures. These larger ice crystals leave behind larger pores upon sublimation, and the larger pores offer less resistance to the flow of water vapor during further sublimation.

INDUSTRIAL APPLICABILITY

The present method provides an improved method for controlling the temperature and/or time at which sub-cooled materials, namely liquids or solutions, nucleate and then freeze. Although this application focuses in part on freeze-drying, a similar problem occurs for any material processing step that involves a nucleated phase transition. Examples of such processes include the crystallization of polymers and metals from melts, crystallization of materials from supersaturated solutions, crystallization of proteins, artificial snow production, food freezing, freeze concentration, fractional crystallization, cryo-preservation, or condensation of vapors to liquids.

The most immediate benefit of controlling the nucleation temperature of a liquid or solution is the ability to control the number and size of the solid domains produced by the phase transition. In freezing water, for example, the nucleation temperature directly controls the size and number of ice crystals formed. Generally speaking, the ice crystals are fewer in number and larger in size when the nucleation temperature is warmer.

The ability to control the number and size of the solid domains produced by a phase transition may provide additional benefits. In a freeze-drying process, for example, the number and size of the ice crystals strongly influences the drying properties of the lyophilized cake. Larger ice crystals produced by warmer nucleation temperatures leave behind larger pores upon sublimation, and the larger pores offer less resistance to the flow of water vapor during subsequent sublimation. Hence, the disclosed system and methods provide a means of increasing primary drying (i.e., sublimation) rates in freeze-drying processes by increasing the nucleation temperature.

Another possible benefit may be realized in applications where sensitive materials are preserved via freezing processes (i.e., cryopreserved). For example, a biological material including but not limited to, mammalian tissue samples (e.g., cord blood, tissue biopsy, egg and sperm cells, etc.), cell lines (e.g., mammalian, yeast, prokaryotic, fungal, etc.) and biological molecules (e.g., proteins, DNA, RNA and subclasses thereof) frozen in an aqueous solution may experience various stresses during the freezing process that may impair the function or activity of the material. Ice formation may physically disrupt the material or create severe changes in the interfacial bonding, osmotic forces, solute concentrations, etc. experienced by the material. Since nucleation controls the structure and kinetics of ice formation, it can significantly influence these stresses. The present system and methods therefore provide unique means of mitigating stresses associated with cryopreservation processes and enhancing the recovery of function or activity from cryopreserved materials. This represents an improvement over conventional nucleation control methods (e.g., seeding or contact with cold surfaces) used to initiate extracellular ice formation in two-step cryopreservation algorithms designed for living cells.

The present methods may be also applied to complex solutions or mixtures containing several constituents both in cryopreservation and lyophilization applications. These formulations are often solutions with an aqueous, organic, or mixed aqueous-organic solvent containing a pharmaceutically active ingredient (e.g., a synthetic chemical, protein, peptide, or vaccine) and optionally, one or more mitigating constituents, including bulking agents that help prevent physical loss of the active ingredient during drying (e.g., dextrose, glucose, glycine, lactose, maltose, mannitol, polyvinyl pyrrolidone, sodium chloride, and sorbitol); buffering agents or toxicity modifiers that help maintain the appropriate environmental pH or toxicity for the active constituent (e.g., acetic acid, benzoic acid, citric acid, hydrochloric acid, lactic acid, maleic acid, phosphoric acid, tartaric acid, and the sodium salts of the aforementioned acids); stabilizing agents that help preserve the structure and function of the active constituent during processing or in its final liquid or dried form (e.g., alanine, dimethylsulfoxide, glycerol, glycine, human serum albumin, polyethylene glycol, lysine, polysorbate, sorbitol, sucrose, and trehalose); agents that modify the glass transition behavior of the formulation (e.g., polyethylene glycol and sugars), and antioxidants that protect the active constituent from degradation (e.g., ascorbate, sodium bisulfite, sodium formaldehyde, sodium metabisulfite, sodium sulfite, sulfoxylate, and thioglycerol).

Since nucleation is typically a random process, a plurality of the same material subjected to identical processing conditions might nucleate at different temperatures. As a result, the properties of those materials that depend on nucleation behavior will likely differ despite the identical processing conditions. The disclosed system and methods provide a means for controlling the nucleation temperatures of a plurality of materials simultaneously and thereby offers a way to increase the uniformity of those product properties that depend on nucleation behavior. In a typical freeze-drying process, for example, the same solution in separate vials may nucleate stochastically over a wide range of temperatures, and as a result, the final freeze-dried products may possess significant variability in critical properties like residual moisture, activity and reconstitution time. By controlling the nucleation temperature via the presently disclosed process, the vial-to-vial uniformity of product properties from a freeze-drying can process can be dramatically improved.

The ability to control the nucleation behavior of a material may also provide substantial benefit in reducing the time necessary to develop an industrial process that hinges upon a normally uncontrolled nucleation event. For example, it often takes many months to develop a successful freeze-drying cycle that can be accomplished in a reasonable amount of time, yields desired product properties within the specified uniformity, and preserves sufficient activity of the active pharmaceutical ingredient (API). By providing a means of controlling nucleation and thereby potentially improving primary drying time, product uniformity, and API activity, the time necessary to develop successful freeze-drying protocols should be dramatically reduced.

In particular, the potential benefits of the controlled nucleation process will provide increased flexibility in specifying the composition of the formulation to be freeze-dried. Since controlled nucleation can better preserve the API during the freezing step, users should be able to minimize the addition of mitigating constituents (e.g., stabilizing agents) to the formulation or chose simpler combinations of formulation constituents to achieve combined stability and processing goals. Synergistic benefits may arise in cases where controlled nucleation minimizes the use of stabilizing agents or other mitigating constituents that inherently lengthen primary dying times (e.g, by decreasing glass transition temperatures of aqueous solutions).

The disclosed methods are particularly well-suited for large scale production or manufacturing operations since it can be conducted using the same equipment and process parameters that can easily be scaled or adapted to manufacture a wide range of products. The process provides for the nucleation of materials using a process where all manipulations can be carried out in a single chamber (e.g., a freeze-dryer) and where the process does not require use of a vacuum, use of additives, vibration, electrofreezing or the like to induce nucleation.

In contrast to the prior art, the present method does not add anything to the lyophilized product. It only requires that the materials, (e.g., liquids in the vials), be held initially at a specified pressure under a gas environment and that the pressure is rapidly reduced to a lower pressure. Any applied gas will be removed from the vials during the lyophilization cycle. The vials or their contents are not contacted or touched with anything except the gas. Simple manipulation of the ambient pressure and gas environment is sufficient on its own to achieve that goal. By relying only on ambient pressure change to induce nucleation, the present method disclosed herein uniformly and simultaneously affects all vials within a freeze-dryer.

The present embodiment is also less expensive and easier to implement and maintain than prior art methods of influencing nucleation in materials in lyophilization applications. The present method enables significantly faster primary drying in lyophilization processes, thereby reducing processing costs for freeze-dried pharmaceuticals. The present method produces much more uniform lyophilized products than prior art methods, thereby reducing product losses and creating barriers to entry for processors unable to meet tighter uniformity specifications. This method achieves these benefits without contaminating the lyophilized product. Greater process control should lead to an improved product and shortened process times.

From the foregoing, it should be appreciated that the present invention thus provides a system and method of lyophilization. Various modifications, changes, and variations of the present methods will be apparent to a person skilled in the art. For example, the means for controlling temperature may be alternate cryogenic based cooling systems or conventional or advanced mechanical refrigeration systems. Likewise, the means to control the pressure and gas atmosphere in the chamber is specifically contemplated to include know pressurization and depressurization techniques. It is to be understood that any such alternate configurations, modifications, changes, and variations are to be included within the purview of this application and the spirit and scope of the claims.

The invention claimed is:

1. A method of lyophilizing a material within a freeze-dryer chamber comprising the steps of:
   pressurizing a gas atmosphere within the freeze-dryer chamber between 7 and 50 psig;
   bringing the material to a temperature near or below a phase transition temperature in the pressurized gas atmosphere;
   rapidly decreasing the pressure to nucleate freezing in the material; and drying the material to produce a dried product having reduced moisture or solvent; wherein the gas atmosphere comprises an inert gas.

2. The method of lyophilizing as set forth in claim 1 wherein the material is selected from the group consisting of: a biopharmaceutical material, a pharmaceutical material, a biological material, or combinations thereof.

3. The method of lyophilizing as set forth in claim 1 wherein the pressurized gas atmosphere comprises a gas selected from the group consisting of: argon, helium, xenon, or mixtures thereof.

4. The method of lyophilizing as set forth in claim 1 wherein the material is brought to a temperature ranging from the phase transition temperature to below the phase transition temperature up to about 40° C. of sub-cooling prior to a step of depressurization.

5. The method of lyophilizing as set forth in claim 1 wherein the pressure is rapidly decreased by about 7 psi or more.

6. The method of lyophilizing as set forth in claim 1 wherein the pressure is rapidly decreased such that an absolute pressure ratio, $P_i/P_f$, is about 1.2 or greater.

7. The method of lyophilizing as set forth in claim 1 wherein the pressure is rapidly decreased at a pressure rate drop, $\Delta P/\Delta t$, greater than about 0.2 psi per second.

8. The method of lyophilizing as set forth in claim 1 wherein the pressure is rapidly decreased in 10 seconds or less.

* * * * *